(12) United States Patent
Berry

(10) Patent No.: US 10,881,531 B2
(45) Date of Patent: Jan. 5, 2021

(54) DUAL EXPANDABLE SPINAL IMPLANT

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 52 days.

(21) Appl. No.: 16/409,149

(22) Filed: May 10, 2019

(65) Prior Publication Data
US 2020/0352738 A1  Nov. 12, 2020

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC .......... *A61F 2/4611* (2013.01); *A61F 2/4455* (2013.01); *A61F 2/442* (2013.01); *A61F 2002/2835* (2013.01); *A61F 2002/30556* (2013.01); *A61F 2002/30579* (2013.01); *A61F 2002/30593* (2013.01); *A61F 2220/0025* (2013.01)

(58) Field of Classification Search
CPC ...... A61F 2/4611; A61F 2/4455; A61F 2/442; A61F 2/447; A61F 2220/0025; A61F 2002/3055; A61F 2002/30523; A61F 2002/2835; A61F 2002/30556; A61F 2002/30579; A61F 2002/30593; A61F 2002/3008; A61F 2002/3052; A61F 2002/30387; A61F 2002/30448; A61F 2002/30492; A61F 2002/30507; A61F 2002/30515; A61F 2002/30538; A61F 2002/30545; A61F 2002/30777; A61F 2002/30878; A61F 2002/30904; A61F 2002/4629; A61F 2002/4677
USPC ........................................... 623/17.11–17.16
See application file for complete search history.

(56) References Cited

U.S. PATENT DOCUMENTS

| | | | |
|---|---|---|---|
| 8,394,129 B2* | 3/2013 | Morgenstern Lopez | A61F 2/447 606/279 |
| 9,155,628 B2* | 10/2015 | Glerum | A61F 2/4455 |
| 10,285,824 B2* | 5/2019 | Robinson | A61F 2/4455 |
| 10,507,116 B2* | 12/2019 | Shoshtaev | A61F 2/4425 |
| 10,527,443 B2* | 1/2020 | White | G01C 21/3626 |

(Continued)

*Primary Examiner* — Pedro Philogene
(74) *Attorney, Agent, or Firm* — Ellenoff Grossman & Schole LLP; James M. Smedley; Alex Korona

(57) ABSTRACT

Apparatus and associated methods relate to a spinal implant configured to expand both vertically and laterally at the same time when wedges coupled by a threaded post drive movable spinal implant endplates radially outward from the longitudinal axis of the threaded post, displacing the wedges and expanding the implant as the threaded post turns. In an illustrative example, the wedges may be a pair of wedges configured with dual inclined planes. The inclined planes may be, for example, disposed both vertically and laterally with respect to the threaded post longitudinal axis, permitting implant expansion both vertically and laterally simultaneously. In some examples, the wedges may be cones. Some embodiments may include a lock adapted to prevent the threaded post from turning. Various examples may advantageously provide improved stability and reduced subsidence, based on increased vertebral body contact area with an implant expanded in place to the desired height and width.

20 Claims, 6 Drawing Sheets

(56) References Cited

U.S. PATENT DOCUMENTS

2008/0177306 A1* 7/2008 Lamborne .......... A61B 17/7067
606/246
2012/0185049 A1* 7/2012 Varela .................. A61F 2/4611
623/17.16

* cited by examiner

DUAL EXPANDABLE SPINAL IMPLANT

TECHNICAL FIELD

Various embodiments relate generally to spinal implants.

BACKGROUND

Spinal implants are medical devices used to treat problems with a patient's spine. A surgeon may install a spinal implant in a patient's spine during spinal surgery. In some examples, a patient may have spinal implant surgery to stabilize the spine, or relieve pain. For example, a patient may suffer from back pain due to spinal damage or deterioration, which may result in spinal instability. In an illustrative example, spinal instability may be a result of injury, or disease.

Some spinal conditions may be treated with surgical removal of a disc or associated tissues, however, when the disc nucleus is removed without subsequent stabilization, the same disabling back pain may reoccur due to persistent inflammation, or instability. In some scenarios, adjacent vertebrae may be fused together through a fusion device implanted between the vertebrae. In addition to fusing the vertebrae together, another surgical goal of spinal implantation may be to distract the vertebrae apart, to prevent the vertebrae from compressing the nerve roots which may cause pain or even paralysis.

In some examples, fusion surgery outcomes may be limited by the vertebral endplate area in contact with a fusion device implanted between the vertebrae. In an illustrative example, placing a spinal implant large enough to stabilize the vertebral bodies within a collapsed disc space may be difficult. In various scenarios, desirable post-surgical spinal stability or subsequent bone growth may be limited by the spinal implant's surface area in contact with the adjacent vertebral endplates.

SUMMARY

Apparatus and associated methods relate to a spinal implant configured to expand both vertically and laterally at the same time when wedges coupled by a threaded post drive movable spinal implant endplates radially outward from the longitudinal axis of the threaded post, displacing the wedges and expanding the implant as the threaded post turns. In an illustrative example, the wedges may be a pair of wedges configured with dual inclined planes. The inclined planes may be, for example, disposed both vertically and laterally with respect to the threaded post longitudinal axis, permitting implant expansion both vertically and laterally simultaneously. In some examples, the wedges may be cones. Some embodiments may include a lock adapted to prevent the threaded post from turning. Various examples may advantageously provide improved stability and reduced subsidence, based on increased vertebral body contact area with an implant expanded in place to the desired height and width.

Various embodiments may achieve one or more advantages. For example, some embodiments may reduce a surgeon's effort installing a spinal implant. This facilitation may be a result of reducing the surgeon's effort adjusting the spinal implant within a collapsed disc space during implant surgery, based on providing a spinal implant designed to expand both vertically and laterally at the same time. In an illustrative example, an embodiment spinal implant designed to expand both vertically and laterally at the same time may permit a surgeon to implant a smaller device between vertebrae, and then expand the implant in situ. Some examples may provide improved implant surgery outcomes. This facilitation may be a result of improved fusion surgery results based on a spinal implant that improves spinal stability and reduces implant subsidence into the vertebral endplates by increasing the area of contact between the spinal implant and the vertebral endplates. Some embodiments may reduce post-surgical spinal pain. Such reduced post-surgical spinal pain may be a result of providing a spinal implant that can be adjusted during surgery to a height and width effective to improve structural stability of the patient's spinal column, thereby helping the implant keep the vertebrae apart to prevent pain due to pressure on the nerve roots. In some embodiments, post-surgical structural stability of the patient's spine may be improved. Such improved spinal stability may be a result of an implant that is expandable both vertically and laterally at the same time, to increase the implant's contact surface area engaged with vertebral bodies in the patient's spine.

Various embodiments may improve spinal fusion surgical outcomes. Such improved surgical outcomes for spinal fusion surgery may be a result of reducing the structural load placed against the weakest parts of the vertebral bodies, based on providing a spinal implant that increases the surface area of contact between the implant and the vertebral bodies to reduce cavitation of the implant into the vertebrae. Some implementations may reduce the risk of damage to the vertebrae. This facilitation may be a result of maintaining the space between the vertebral bodies separated by the implant, based on improved post-surgical bone growth fusion resulting from an increased area of contact between the spinal implant and the vertebral endplates. In some examples, a spinal implant expandable both vertically and laterally at the same time may help solve the problem of placing an implant in a collapsed disc space by allowing a surgeon to implant a smaller spinal implant device between the vertebrae, and then expanding the smaller spinal implant in situ, effectively expanding the spinal implant to a size large enough to distract the vertebral posterior elements and relieve pressure on the nerve root. Various embodiments may improve post-surgical fusion surgery bone growth. This facilitation may be a result of a spinal implant expandable both vertically and laterally at the same time to increase the amount of bone graft material that may be used with the implant, based on increasing the area of graft material that is able to contact the vertebral endplates.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, illustrative usage of an exemplary vertically and laterally expandable spinal implant configured with a pair of bi-planar wedges adapted to drive movable spinal implant endplates radially outward from the longitudinal axis of a threaded post, displacing the wedges as the threaded post turns, is briefly introduced with reference to FIG. 1. Then, with reference to FIGS. 2-10, the discussion turns to exemplary embodiments that illustrate the design and operation of exemplary vertically and laterally expandable spinal implant implementations. Specifically, various views of an exemplary vertically and laterally expandable spinal implant depicted in illustrative configurations are disclosed, to explain improvements in spinal implant design.

Figure 1:
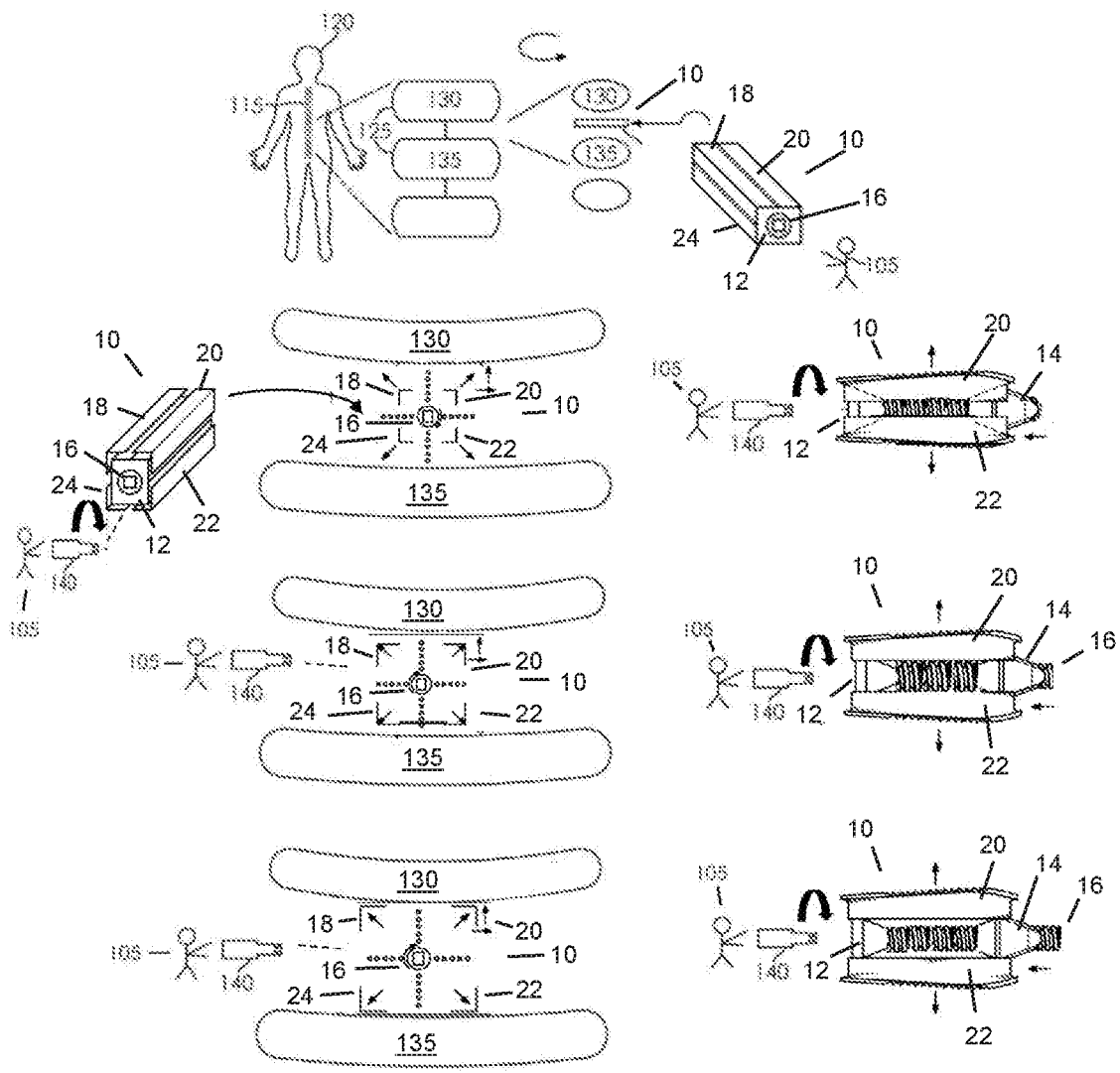
FIG. 1 depicts an illustrative operational scenario wherein a surgeon implants an exemplary spinal implant configured to expand both vertically and laterally at the same time when wedges coupled by a threaded post drive movable spinal implant endplates radially outward from the longitudinal axis of the threaded post, displacing the wedges and expanding the implant as the threaded post turns.

FIG. 1 depicts an illustrative operational scenario wherein a surgeon implants an exemplary spinal implant configured to expand both vertically and laterally at the same time when wedges coupled by a threaded post drive movable spinal implant endplates radially outward from the longitudinal axis of the threaded post, displacing the wedges and expanding the implant as the threaded post turns. In FIG. 1, the surgeon 105 inserts the spinal implant 10 within the spine 115 of the patient 120. In the depicted example, the surgeon 105 inserts the spinal implant 10 between the pair of vertebrae 125. In the illustrated example, the surgeon 105 inserts the spinal implant 10 between superior vertebral endplate 130 and inferior vertebral endplate 135 of the pair of vertebrae 125 in the patient 120 spine 115. In the illustrated example, the surgeon 105 rotationally drives spinal implant 10 threaded post 16 with spinal implant installation tool 140. In the illustrated embodiment, the threaded post 16 axially couples the posterior wedge 12 to the anterior wedge 14. In the depicted embodiment, the threaded post 16 is configured to spin within the posterior wedge 12 and the anterior wedge 14. In the depicted example, the anterior wedge 14 moves axially along the threaded post 16 toward the posterior wedge 12, as the surgeon 105 turns the threaded post 16. In the depicted example, the spinal implant 10 includes four movable endplates 18, 20, 22, and 24, arranged between the posterior wedge 12 and the anterior wedge 14. In the illustrated embodiment, each endplate 18, 20, 22, and 24 is configured with an interior angled face slidably resting on the posterior wedge 12 and the anterior wedge 14. In the depicted embodiment, the posterior wedge 12 and the anterior wedge 14 are both bi-planar wedges, configured such that each wedge includes two inclined plane wedge faces. In the illustrated embodiment, each of the posterior wedge 12 and the anterior wedge 14 include a first wedge face with an incline disposed vertically with respect to the threaded post 16 longitudinal axis. In the depicted embodiment, each of the posterior wedge 12 and the anterior wedge 14 also include a second wedge face with an incline disposed laterally with respect to the threaded post 16 longitudinal axis. In the depicted example, the anterior wedge 14 is pulled posteriorly toward the posterior wedge 12 as the surgeon 105 turns the threaded post 16. In the illustrated embodiment, the action of pulling the anterior wedge 14 toward the posterior wedge 12 forces the endplates 18, 20, 22, and 24 to ride against the wedges. In the depicted embodiment, the endplates 18, 20, 22, and 24 are forced further apart from one another by riding against the anterior wedge 14 and the posterior wedge 12. In the illustrated embodiment, as the threaded post 16 turns, the moving endplates 18, 20, 22, and 24 expand the spinal implant 10 both vertically and laterally at the same time, because the anterior wedge 14 and posterior wedge 12 are bi-planar.

In the depicted example, the threaded post 16 is able to spin within both the posterior wedge 12 and the anterior wedge 14. In the illustrated example, the threaded post 16 is rotatably captured within the posterior wedge 12 so that it can only spin, but cannot move longitudinally or laterally in reference to the posterior wedge 12. In an illustrative example, the threaded portion of the threaded post 16 may not engage the posterior wedge 12. In the illustrated embodiment, the threaded portion of the threaded post 16 engages with the threaded portion of the anterior wedge 14. In the depicted example, the threaded post 16 moves the anterior wedge 14 axially along the threaded post 16 threads as the threaded post 16 spins. In an illustrative practical example, the anterior wedge 14 moves towards the posterior wedge 12 as the threaded post 16 turns.

In the depicted example, both the anterior 14 and posterior wedges 12 have angular, or wedged, faces in two planes. In the illustrated embodiment, the superior and inferior faces of the anterior wedge 14 and the posterior wedge 12 are at an angle to one another. In addition, the lateral faces of the of the anterior wedge 14 and the posterior wedge 12 are also at an angle to one another. In the illustrated embodiment, the endplates 18, 20, 22, and 24 are arranged between the anterior wedge 14 and posterior wedge 12. In the depicted example, each endplate 18, 20, 22, and 24 has an interior angled face. In the illustrated example, the interior angled faces of the endplates 18, 20, 22, and 24 rest upon the angled faces of the anterior wedge 14 and the posterior wedge 12. In an example illustrative of the similar endplate 20, 22, and 24 structures, the upper left endplate 18 has four interior angled faces. For example, one lateral, posterior angled face rests against the lateral face of the posterior wedge 12, while the inferior, posterior angled face of the upper left endplate 18 rests against the superior face of the posterior wedge 12. Correspondingly, the lateral, anterior angled face rests against the lateral face of the anterior wedge 14, while the inferior, anterior angled face of the upper left endplate 18 rests against the superior face of the anterior wedge 14.

In the illustrated example, as the threaded post 16 is turned, the threaded post 16 pulls the anterior wedge 14 posteriorly toward the posterior wedge 12, forcing the endplates 18, 20, 22, and 24 to ride against the wedges, which drive the endplates 18, 20, 22, and 24 further apart from one another. In the depicted example, because the anterior 14 and posterior wedges 12 are bi-planar, the movable endplates 18, 20, 22, and 24 expand the spinal implant 10 both vertically and laterally at the same time, as the threaded post 16 turns.

In some embodiments, the wedges may be cones. In various designs, the wedges may be spheres. In various embodiments, the endplates may be made of a different material than the wedges. Some embodiments may include endplates aligned with pins. Various embodiment implementations may include endplates aligned with dovetail tabs extending between the endplates. In some designs, the wedges may include a dove tail member running along the corners of the wedge's angular faces, wherein the endplates may have a corresponding, mating dovetail. Some embodiments may include a locking mechanism configured to prevent the threaded post from turning.

Figure 2:
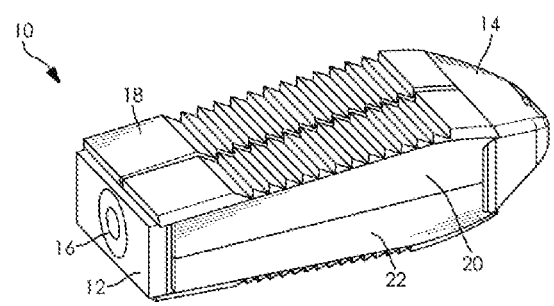
FIG. 2 depicts a top, rear perspective view of an embodiment spinal implant in an illustrative unexpanded configuration.

FIG. 2 depicts a top, rear perspective view of an embodiment spinal implant in an illustrative unexpanded configuration. In FIG. 2, the exemplary unexpanded spinal implant 10 includes the posterior wedge 12 axially coupled with the anterior wedge 14 by the threaded post 16. In the illustrated embodiment, the upper left endplate 18 rests against the posterior wedge 12 superior face and the posterior wedge 12 left lateral face. In the depicted embodiment, the upper left endplate 18 also rests against the anterior wedge 14 superior face and the anterior wedge 14 left lateral face. In the illustrated embodiment, the exemplary spinal implant 10 includes a lower left endplate resting against the posterior wedge 12 inferior face and the posterior wedge 12 left lateral face. In the depicted example, the lower left endplate is obscured from view. In the depicted embodiment, the lower left endplate also rests against the anterior wedge 14 inferior face and the anterior wedge 14 left lateral face. In the illustrated embodiment, the upper right endplate 20 rests against the posterior wedge 12 superior face and the posterior wedge 12 right lateral face. In the depicted embodiment, the upper right endplate 20 also rests against the anterior wedge 14 superior face and the anterior wedge 14 right lateral face. In the illustrated embodiment, the lower right endplate 22 rests against the posterior wedge 12 inferior face and the posterior wedge 12 right lateral face. In the depicted embodiment, the lower right endplate 22 also rests against the anterior wedge 14 inferior face and the anterior wedge 14 right lateral face.

Figure 3:
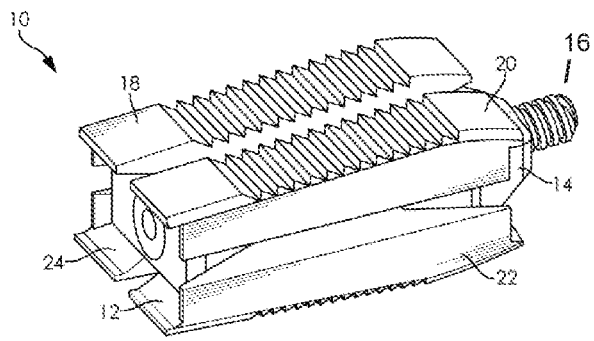
FIG. 3 depicts a top, rear perspective view of an embodiment spinal implant in an illustrative expanded configuration.

FIG. 3 depicts a top, rear perspective view of an embodiment spinal implant in an illustrative expanded configuration. In FIG. 3, the embodiment spinal implant 10 is depicted in an exemplary partially expanded configuration illustrating the endplates 18, 20, 22, and 24 radially displaced from the threaded post 16 longitudinal axis. In the illustrated embodiment, the endplates 18, 20, 22, and 24 are radially displaced from the threaded post 16 longitudinal axis as a result of the anterior wedge 14 moving toward the posterior wedge 12, as the threaded post 16 was turned, to expand the spinal implant 10 both vertically and laterally at the same time. In the illustrated example, the threaded post 16 is visible beyond the end of the anterior wedge 14.

Figure 4:
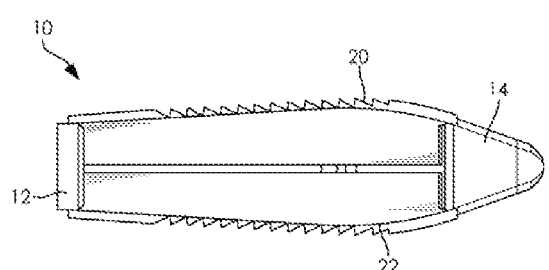
FIG. 4 depicts a side view of an embodiment spinal implant in an illustrative unexpanded configuration.

FIG. 4 depicts a side view of an embodiment spinal implant in an illustrative unexpanded configuration. In FIG. 4, the depicted side view of the exemplary unexpanded spinal implant 10 includes the posterior wedge 12 axially coupled with the anterior wedge 14 by a threaded post. In the depicted example, the threaded post is obscured from view by the upper right endplate 20, the lower right endplate 22, and the anterior wedge 14.

Figure 5:
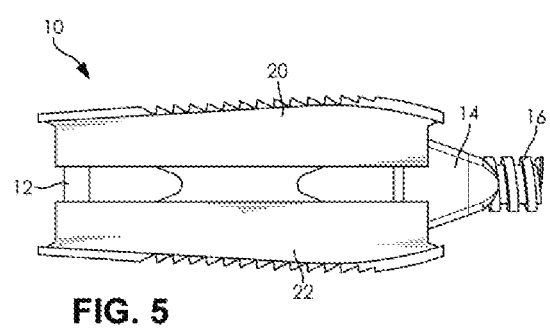
FIG. 5 depicts side view of an embodiment spinal implant in an illustrative expanded configuration.

FIG. 5 depicts side view of an embodiment spinal implant in an illustrative expanded configuration. In FIG. 5, the depicted side view of the exemplary partially expanded spinal implant 10 includes the posterior wedge 12 axially coupled with the anterior wedge 14 by the threaded post 16. In the illustrated example, the threaded post 16 is visible beyond the end of the anterior wedge 14. In the depicted example, the upper right endplate 20 and the lower right endplate 22 are radially displaced from the threaded post 16 longitudinal axis as a result of the anterior wedge 14 moving toward the posterior wedge 12, as the threaded post 16 was turned.

Figure 6:
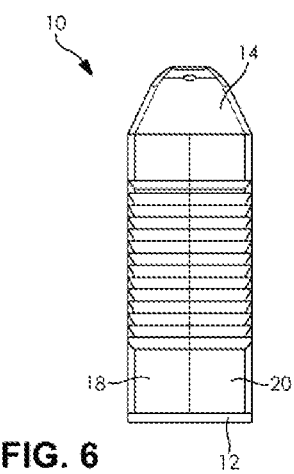
FIG. 6 depicts a top view of an embodiment spinal implant in an illustrative unexpanded configuration.

FIG. 6 depicts a top view of an embodiment spinal implant in an illustrative unexpanded configuration. In FIG. 6, the depicted top view of the exemplary unexpanded spinal implant 10 includes the posterior wedge 12 axially coupled with the anterior wedge 14 by a threaded post. In the depicted example, the threaded post is obscured from view by the upper right endplate 20, the upper left endplate 18, and the anterior wedge 14.

Figure 7:
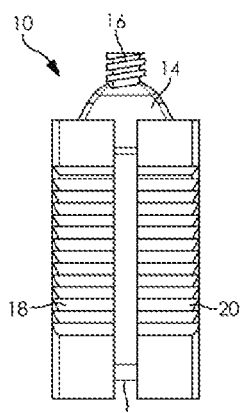
FIG. 7 depicts a top view of an embodiment spinal implant in an illustrative expanded configuration.

FIG. 7 depicts a top view of an embodiment spinal implant in an illustrative expanded configuration. In FIG. 7, the depicted top view of the exemplary partially expanded spinal implant 10 includes the posterior wedge 12 axially coupled with the anterior wedge 14 by the threaded post 16. In the illustrated example, the threaded post 16 is visible beyond the end of the anterior wedge 14. In the depicted example, the upper right endplate 20 and the upper left endplate 18 are radially displaced from the threaded post 16 longitudinal axis as a result of the anterior wedge 14 moving toward the posterior wedge 12, as the threaded post 16 was turned.

Figure 8:
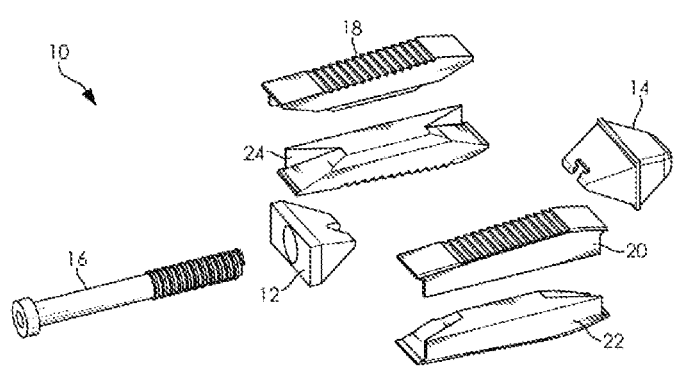
FIG. 8 depicts a top, rear perspective view of an embodiment spinal implant in an illustrative exploded configuration.

FIG. 8 depicts a top, rear perspective view of an embodiment spinal implant in an illustrative exploded configuration. In FIG. 8, the depicted top, rear perspective view of the exemplary spinal implant 10 in the illustrated exploded configuration includes the threaded post 16, the posterior wedge 12, the anterior wedge 14, the upper left endplate 18, the lower left endplate 24, the upper right endplate 20, and the lower right endplate 22. In the illustrated embodiment, the depicted posterior wedge 12 superior face and right lateral face are visible. In the depicted embodiment, the illustrated anterior wedge 14 superior face and the anterior wedge 14 right lateral faces are visible. In the depicted example, the anterior wedge 14 includes two right lateral faces. In the illustrated example, the anterior wedge 14 includes two left lateral faces that are obscured from view. In some embodiments, the anterior wedge 14 may have only one left lateral face. In various embodiments, the anterior wedge 14 may have only one right lateral face.

Figure 9:
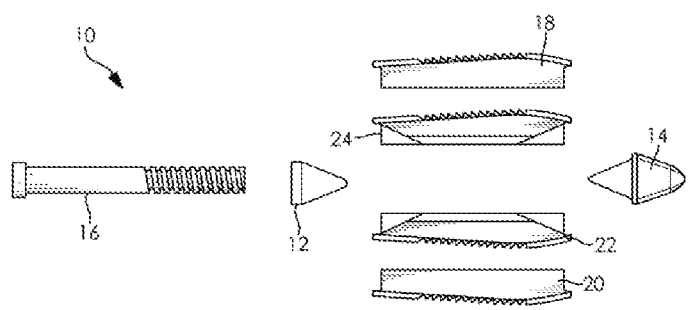
FIG. 9 depicts a side view of an embodiment spinal implant in an illustrative exploded configuration.

FIG. 9 depicts a side view of an embodiment spinal implant in an illustrative exploded configuration. In FIG. 9, the depicted side view of the exemplary spinal implant 10 in the illustrated exploded configuration includes the threaded post 16, the posterior wedge 12, the anterior wedge 14, the upper left endplate 18, the lower left endplate 24, the upper right endplate 20, and the lower right endplate 22. In the illustrated embodiment, the depicted posterior wedge 12 right lateral face is visible. In the depicted embodiment, the illustrated anterior wedge 14 right lateral faces are visible. In the depicted example, the anterior wedge 14 includes two right lateral faces. In the illustrated example, the anterior wedge 14 includes two left lateral faces that are obscured from view. In some embodiments, the anterior wedge 14 may have only one left lateral face. In various embodiments, the anterior wedge 14 may have only one right lateral face.

Figure 10:
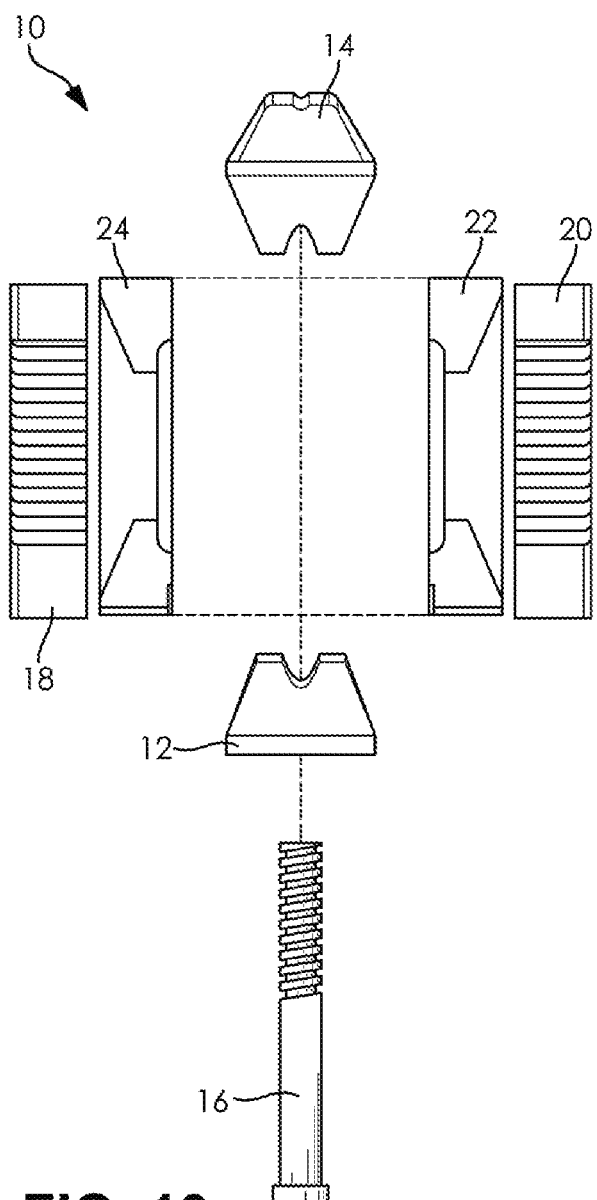
FIG. 10 depicts a top view of an embodiment spinal implant in an illustrative exploded configuration.

FIG. 10 depicts a top view of an embodiment spinal implant in an illustrative exploded configuration. In FIG. 10, the depicted top view of the exemplary spinal implant 10 in the illustrated exploded configuration includes the threaded post 16, the posterior wedge 12, the anterior wedge 14, the upper left endplate 18, the lower left endplate 24, the upper right endplate 20, and the lower right endplate 22. In the illustrated embodiment, the depicted posterior wedge 12 superior face is visible. In the depicted embodiment, the depicted posterior wedge 12 inferior face is obscured from view. In the depicted embodiment, the illustrated anterior wedge 14 superior faces are visible. In the depicted example, the anterior wedge 14 includes two superior faces. In the illustrated example, the anterior wedge 14 includes two inferior faces that are obscured from view.

Although various embodiments have been described with reference to the Figures, other embodiments are possible. For example, various embodiment vertical and lateral expandable spinal implant designs may include a posterior wedge and anterior wedge that are adapted to receive a threaded post axially between the two. Some embodiment implant implementations may also have four separate longitudinal moveable endplates. In an illustrative example, an implant implementation having four longitudinal moveable endplates may be configured with all four endplates aligned parallel to the threaded post. In some embodiments, each endplate may also have corresponding angled faces which mate to the wedges. In some embodiment implementations, the wedges may include wedges in two planes, both vertically and laterally. In an exemplary usage scenario, as the threaded post turns, the threaded post draws the wedges toward each other. In an illustrative example, the turning threaded post drawing the wedges toward each other forces the wedges against the endplates. In some scenarios, the wedges are forced outward, both vertically and horizontally, as the wedges are forced against the endplates by the turning threaded post drawing the wedges toward each other.

Various embodiments of the present invention generally relate to spinal implants, and more specifically, but not exclusively, concern a vertically and laterally expandable vertebral implant.

In some scenarios, persistent, often disabling, back pain can arise by disruption of the disc annulus, chronic inflammation of the disc, or relative instability of the vertebral bodies surrounding a given disc, such as might occur due to a degenerative disease. In an example illustrative of some severe cases, some form of mechanical limitation to the movement of the vertebrae on either side of the subject disc may be necessary. In such cases, the disc tissue may be irreparably damaged, thereby necessitating removal of the entire disc. However, when the disc nucleus is removed without subsequent stabilization, the same disabling back pain may reoccur due to persistent inflammation and/or instability.

Various prior art approaches illustrative of previous attempts to stabilize the adjacent vertebral bodies following excision of the disc material have been developed. In one prior art approach, two adjacent vertebrae are fused together through a fusion device that is implanted between the vertebrae, however, in addition to fusing the vertebrae together, another surgical goal is to distract the vertebrae apart. This is because often times the disc separating the two vertebrae has collapsed or shrunk. The shrinking of the disc can cause the vertebrae to compress the nerve roots which extend between the posterior elements. The pressure on the nerve roots can cause pain or even paralysis. Therefore, part of the reason for inserting an implant between the vertebrae is to distract the vertebrae apart, and such a prior art approach of simply fusing the vertebrae together through a fusion device that is implanted between the vertebrae does not distract the vertebrae apart.

Some prior art spinal implant devices are simply a solid spacer, intended to wedge the vertebrae apart, or hold the spacer after the vertebrae are distracted by means of a separate instrument. Other prior art spinal implant devices expand themselves in order to distract the vertebrae. Some of these prior art spinal implant devices are hinged, so that only one end of the implant expands. In such a prior art device design, the vertebrae are distracted at an angle from one another, and not parallel to each other. For example, a hinged spinal implant, distracting vertebra at an angle that is not parallel to each other, does not alleviate the primary problem of distracting the vertebral posterior elements and relieving pressure on the nerve root. In an illustrative example, part of the problem with placing an implant in a collapsed disc space is getting a large enough implant into the space, and a hinged device does not allow this to happen.

Some examples illustrative of various prior art spinal implants can be expanded in a manner to create parallel distraction, distracting the disc space in the posterior area, and relieving pressure on the nerve roots. Although such prior art spinal implants may be inserted by a surgeon into a collapsed disc space in an unexpanded configuration, and then expanded in situ to the desired height, patients receiving these prior art spinal implants may suffer from a lack of stability created by the expansion in a single dimension. In an illustrative example, for almost any structural device, the height to width ratio is a crucial factor in determining the device's structural stability. For example, the wider the base a structure has, the more inherent stability the structure has. Contrarily, as these implants expand only vertically, they grow taller, but not wider, thereby decreasing overall stability.

In some examples, desirable spinal implant design goals may include stabilizing the vertebrae in order to create a bony fusion between the vertebra in contact with the spinal implant. However, some prior art spinal implant designs have drawbacks that lower the spinal fusion rates. Among these prior art spinal implant design drawbacks, one such design flaw is that the spinal implants subside into the vertebral endplates, thereby reducing the spacing between the vertebral bodies. With some prior art fusion devices, and even some prosthetic devices, a large portion of the load is placed against the weakest part of the vertebral body which can lead to cavitation of the device into the surrounding vertebral endplates, with subsequent collapse of the inner discal space and even damage of the vertebrae itself. Another frequent cause for subsidence in some prior art spinal implant examples is created by having a small area of contact between an exemplary prior art spinal implant and the surrounding vertebral endplates. In an example illustrative of various prior art spinal implants' usage, less contact surface area between the spinal implant and the vertebral endplates may contribute to a greater risk of the spinal implant's subsidence into the vertebral endplates.

Although desirable spinal implant design goals may include providing stability that is crucial to the success of a fusion operation, some prior art spinal implant designs may leave patients suffering from a lack of stability after implantation surgery. In an example illustrative of some spinal implantation procedures, the spinal implant must be securely fixated to the vertebral bodies in order to ensure that no movement occurs between the vertebral bodies and the spinal implant. For example, if movement does occur between the vertebral bodies and the spinal implant, the bone may not properly fuse, creating stability problems. In addition, some prior art spinal implant designs limit the amount of graft material which may be able to be used with the implant, limiting the bone growth between vertebrae and reducing the chance of adequate stability. In an illustrative example, the chance of good, solid bone growth between two vertebrae are improved when the area of graft material that is able to contact the vertebral endplates is increased.

Some prior art spinal implant designs include a structure positioning the majority of the implant over the harder cortical bone of the apophyseal ring of the vertebrae in order to reduce the chances of subsidence. However, with such prior art spinal implant designs, the spinal implant may be made from multiple separate components that are individually assembled together within the disc space. As should be appreciated, assembling such a prior art spinal implant in the disc space can be rather difficult. Such prior art spinal implants also tend to lack a stiff central body, which is essential to the stability of the implant as well as the entire fusion construct.

In various embodiments of the present invention, an embodiment vertical and lateral expandable spinal implant includes a posterior wedge and anterior wedge that are adapted to receive a threaded post axially between the posterior wedge and anterior wedge. In some embodiments, the spinal implant also has four separate longitudinal moveable endplates. In an illustrative example, all four spinal implant endplates are aligned parallel to the threaded post. In various embodiment designs, each of the four spinal implant endplates also has corresponding angled faces which mate to the wedges. In various embodiments, the wedges are wedges in two planes, both vertically and laterally. In an illustrative example, as the threaded post turns, the threaded post draws the wedges toward each other. The threaded post drawing the wedges toward each other forces the wedges against the spinal implant endplates, forcing them outward, both vertically and horizontally, allowing the spinal implant to be inserted in an unexpanded, smaller configuration. As the spinal implant expands, it does so with the implant endplates moving parallel to one another, both vertically and laterally. Thereby, the spinal implant can distract the two vertebrae, relieving the pressure on the nerve root. Furthermore, the endplates expand laterally. This creates a wider base for the spinal implant, improving the spinal implant stability. Additionally, by expanding wider laterally, the spinal implant endplates can seat closer to the stronger apophyseal ring of the vertebrae, reducing the risk of subsidence.

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments. elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of" In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. An apparatus, comprising:
a spinal implant configured to expand both vertically and laterally at the same time, comprising:
a first wedge and second wedge, each comprising a superior angled face, and inferior angled face, a left lateral angled face, and a right lateral angled face, wherein the superior angled face meets the inferior angled face at a horizontal plane of each wedge to form a horizontally disposed wedge extending between the left lateral angled face and the right lateral angled face;
a threaded post in the coupling the first wedge to the second wedge, wherein the threaded post is rotatably retained by the first wedge and a threaded aperture configured in the second wedge; and,
a plurality of endplates, wherein each endplate of the plurality of endplates has a first end that is slidably engaged with the horizontally disposed wedge of the first wedge and a second end that is slidably engaged with the horizontally disposed wedge of the second wedge and end that us slidably engaged with the horizontally disposed wedge of the second wedge and each of the superior faces and each the inferior faces is slidably engaged with the two endplates.

2. The apparatus of claim 1, wherein the left lateral angled face and the right lateral angled face are angled inward toward a center portion of each of the wedges.

3. The apparatus of claim 1, wherein the left lateral angled face and the right lateral angled face are substantially triangular in shape.

4. The apparatus of claim 1, wherein each of the endplates are formed with interior angled faces that are slidably engaged with the first and second wedges.

5. The apparatus of claim 1, wherein the first wedge is disposed at the first threaded post end, and the second threaded post end rotatably engages the second wedge threaded aperture.

6. The apparatus of claim 1, wherein the threaded post is rotatably retained by the first wedge such that the threaded post can spin within the first wedge without changing the first wedge longitudinal displacement with respect to the first threaded post end.

7. The apparatus of claim 1, wherein the apparatus further comprises a locking mechanism configured to prevent the threaded post from turning.

8. The apparatus of claim 1, wherein each of the plurality of endplates further comprise an interior angled face configured to rest upon the first wedge and the second wedge.

9. The apparatus of claim 1, wherein the first wedge and the second wedge are both unitary shaped blocks.

10. The apparatus of claim 9, wherein the first wedge is configured with a flat face opposite of the horizontally disposed wedge and the second wedge is configured with a substantially domed projection extending opposite the horizontally disposed wedge.

11. The apparatus of claim 1, wherein each of the horizontally disposed wedges are formed with a notch extending through the superior and inferior angled faces to accommodate the threaded post.

12. An apparatus, comprising:
a spinal implant configured to expand both vertically and laterally at the same time, comprising:
a first bi-planar wedge, having at least one angular wedge face vertically disposed in a first plane, and at least one angular wedge face laterally disposed in a second plane;
a second bi-planar wedge, having at least one angular wedge face vertically disposed in a first plane, and at least one angular wedge face laterally disposed in a second plane, wherein the second bi-planar wedge is coupled with the first bi-planar wedge by a threaded post rotatably retained by the first bi-planar wedge and a threaded aperture configured in the second bi-planar wedge; and, a plurality of movable endplates, wherein each endplate of the plurality of endplates is slidably engaged with at least one vertically disposed bi-planar wedge face and at least one laterally disposed bi-planar wedge face; and, wherein the plurality of endplates include interior angled faces adapted to slidably engage with the first bi-planar wedge and the second bi-planar wedge, to drive the movable spinal implant endplates radially outward from the longitudinal axis of the threaded post, displacing the wedges and expanding the implant as the threaded post turns.

13. The apparatus of claim 12, wherein the apparatus further comprises a locking mechanism configured to prevent the threaded post from turning.

14. The apparatus of claim 12, wherein the first bi-planar wedge is disposed at the first threaded post end, and second threaded post end rotatably engages the second bi-planar wedge threaded aperture.

15. The apparatus of claim 12, wherein at least one endplate pair of the plurality of moveable endplates further comprises a dovetail tab extending between the endplate pair.

16. The apparatus of claim 12, wherein the first bi-planar wedge or the second bi-planar wedge further comprise a dove tail member running along the corners of the wedge's angular faces, and wherein at least one of the plurality of endplates may have a corresponding, mating dovetail.

17. An apparatus, comprising:
a spinal implant configured to expand both vertically and laterally at the same time, comprising:
a first bi-planar wedge, having at least one angular wedge face vertically disposed in a first plane, and at least one angular wedge face laterally disposed in a second plane;

a second bi-planar wedge, having at least one angular wedge face vertically disposed in a first plane, and at least one angular wedge face laterally disposed in a second plane, wherein the second bi-planar wedge is coupled with the first bi-planar wedge by a threaded post rotatably retained by the first bi-planar wedge and a threaded aperture configured in the second bi-planar wedge; and, four movable endplates, wherein each of the four moveable endplates is slidably engaged with at least one vertically disposed bi-planar wedge face and at least one laterally disposed bi-planar wedge face; and, wherein each of the four moveable endplates include interior angled faces adapted to slidably engage with the first bi-planar wedge and the second bi-planar wedge, to drive the movable spinal implant endplates radially outward from the longitudinal axis of the threaded post, displacing the wedges and expanding the implant both vertically and laterally at the same time as the threaded post turns.

18. The apparatus of claim 17, wherein the threaded post is rotatably retained by the first bi-planar wedge such that the threaded post can spin within the first bi-planar wedge without changing the first bi-planar wedge longitudinal displacement with respect to the first threaded post end.

19. The apparatus of claim 17, wherein the apparatus further comprises a locking mechanism configured to prevent the threaded post from turning.

20. The apparatus of claim 17, wherein the first bi-planar wedge or the second bi-planar wedge further comprise a dove tail member running along the corners of the wedge's angular faces, and wherein at least one of the plurality of endplates may have a corresponding, mating dovetail.

* * * * *